United States Patent [19]

Sobolik

[11] Patent Number: 5,261,398
[45] Date of Patent: Nov. 16, 1993

[54] DENTAL EYE SHIELD WITH LINK MOUNTING FEET FOR ATTACHING TO MASK

[76] Inventor: Barbara L. Sobolik, 13704 Lincoln St., Grand Haven, Mich. 49417

[21] Appl. No.: 858,039

[22] Filed: Mar. 26, 1992

[51] Int. Cl.5 .............. A62B 18/08; A62B 18/02; A61F 11/00; A61F 9/02
[52] U.S. Cl. ............. 128/206.23; 128/201.17; 128/205.25; 128/857; 2/427
[58] Field of Search ........ 128/857, 858, 863, 201.15, 128/201.17, 205.25, 206.18, 206.23, 207.13, 917; 2/15, 427, 9, 428, DIG. 7; 433/136

[56] References Cited

U.S. PATENT DOCUMENTS

| | | | |
|---|---|---|---|
| 781,516 | 1/1905 | Guthrie, Jr. | 128/206.18 |
| 1,191,274 | 7/1916 | Brayton | 128/201.15 |
| 2,372,834 | 4/1945 | Kish | 128/207.13 |
| 2,435,653 | 2/1948 | Maurer | 128/207.13 |
| 2,792,000 | 5/1957 | Richardson | 128/207.13 |
| 4,944,294 | 7/1990 | Borek, Jr. | 128/206.19 |
| 4,966,140 | 10/1990 | Herzberg | 128/206.19 |
| 4,969,473 | 11/1990 | Bothwell | 128/863 |
| 5,020,533 | 6/1991 | Hubbard et al. | 128/857 |
| 5,138,714 | 8/1992 | Smith | 128/863 |
| 5,150,703 | 9/1992 | Hubbard et al. | 128/206.23 |
| 5,159,938 | 11/1992 | Laughlin | 128/207.13 |

Primary Examiner—Edgar S. Burr
Assistant Examiner—Kimberly L. Asher
Attorney, Agent, or Firm—Leon Gilden

[57] ABSTRACT

A shield is arranged for mounting to an individual's nose to accommodate conventional eyeglasses and the like and to protect an individual's eyes relative to flying debris during a dental procedure. The shield structure is arranged for securement to a gas administering mask structure.

2 Claims, 4 Drawing Sheets

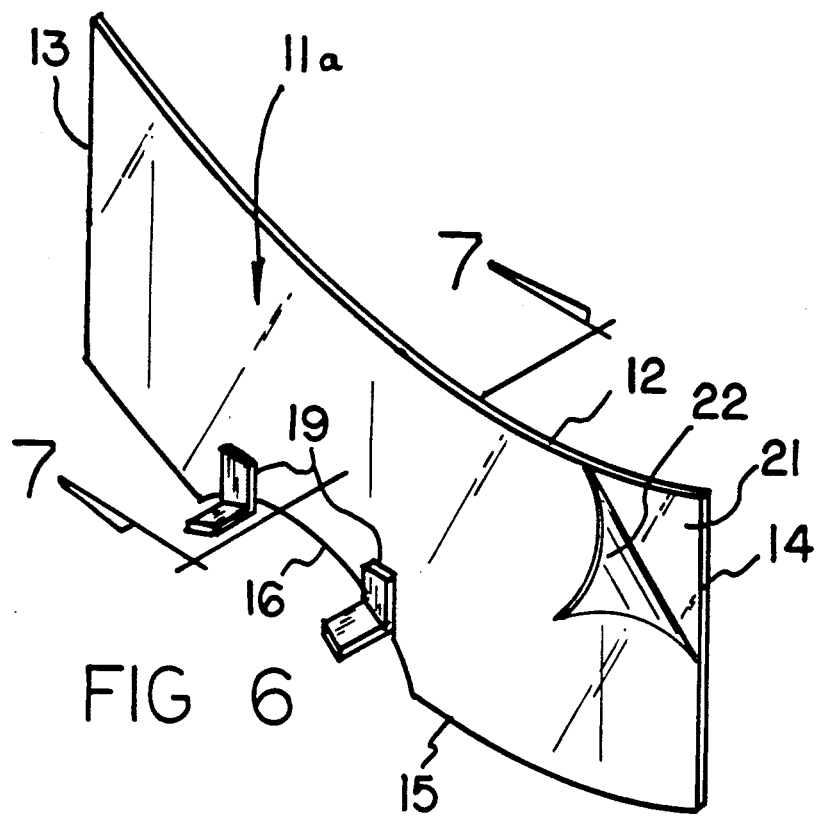
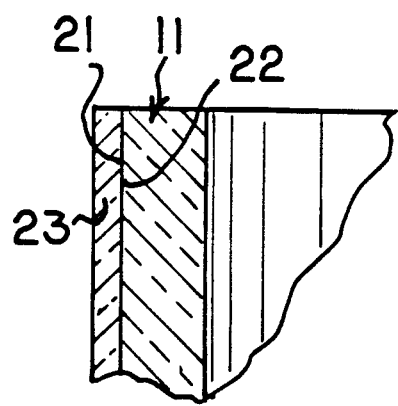
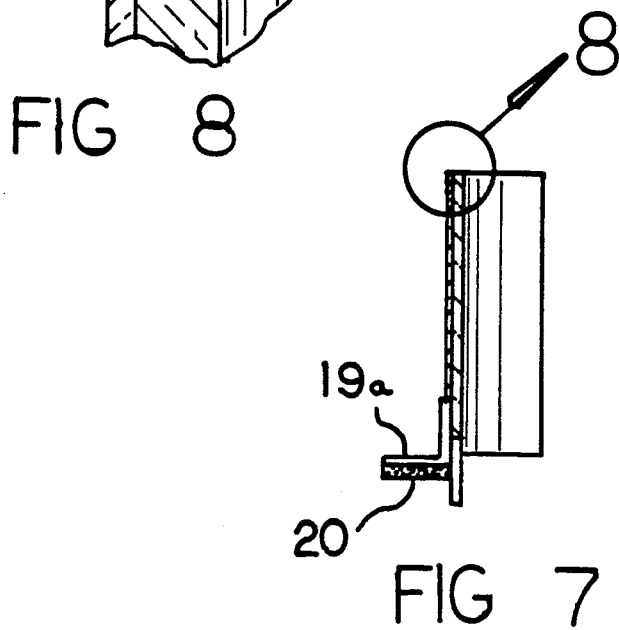

DENTAL EYE SHIELD WITH LINK MOUNTING FEET FOR ATTACHING TO MASK

BACKGROUND OF THE INVENTION

1. Field of the Invention

The field of invention relates to shield structure, and more particularly pertains to a new and improved dental eye shield apparatus wherein the same is arranged to afford protection to an individual's eyes during a dental procedure.

2. Description of the Prior Art

Shields of various types are available in the prior art to accommodate various medical and work related tasks. Such apparatus is exemplified in U.S. Pat. No. 4,955,394 to Dendean wherein a protective face shield is arranged to effect covering of an individual's entire facial region.

U.S. Pat. No. 4,779,291 to Russell sets forth an eyeglass-type eye shield structure.

The U.S. Pat. No. 4,889,490 to Jenkinson sets forth a dental mask arranged to overlie in surrounding relationship an individual's mouth portion during a dental procedure.

U.S. Pat. No. 4,944,294 to Borek sets forth a face mask with an anti-fog shield mounted to an upper portion of the face mask structure.

As such, it may be appreciated that there continues to be a need for a new and improved dental eye shield apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of eye shield apparatus now present in the prior art, the present invention provides a dental eye shield apparatus wherein the same is arranged for mounting to an individual's nose and securing a nasal mask thereto. As such, the general purpose of the present invention, which will be described subsequently in greater detail, is to provide a new and improved dental eye shield apparatus which has all the advantages of the prior art eye shield apparatus and none of the disadvantages.

To attain this, the present invention provides a shield arranged for mounting to an individual's nose to accommodate conventional eyeglasses and the like and to protect an individual's eyes relative to flying debris during a dental procedure. The shield structure is arranged for securement to a gas administering mask structure.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental eye shield apparatus which has all the advantages of the prior art eye shield apparatus and none of the disadvantages.

It is another object of the present invention to provide a new and improved dental eye shield apparatus which may be easily and efficiently manufactured and marketed.

It is a further object of the present invention to provide a new and improved dental eye shield apparatus which is of a durable and reliable construction.

An even further object of the present invention is to provide a new and improved dental eye shield apparatus which is susceptible of a low cost of manufacture with regard to both materials and labor, and which accordingly is then susceptible of low prices of sale to the consuming public, thereby making such dental eye shield apparatus economically available to the buying public.

Still yet another object of the present invention is to provide a new and improved dental eye shield apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is an isometric illustration of a modified aspect of the shield structure of the invention.

FIG. 7 is an orthographic view, taken along the lines 7—7 of FIG. 6 in the direction indicated by the arrows.

FIG. 8 is an orthographic cross-sectional illustration of section 8 as set forth in FIG. 7.

DESCRIPTION OF THE PREFERRED EMBODIMENT

Figure 1:
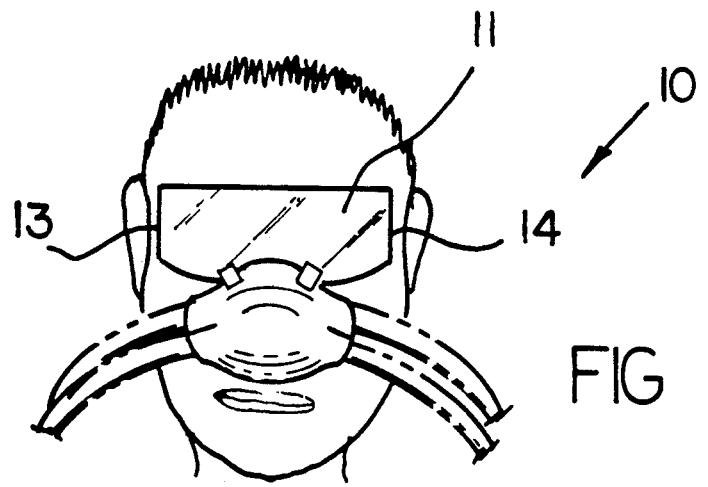
FIG. 1 is an orthographic view, taken in elevation, of the invention in use.
Figure 2:
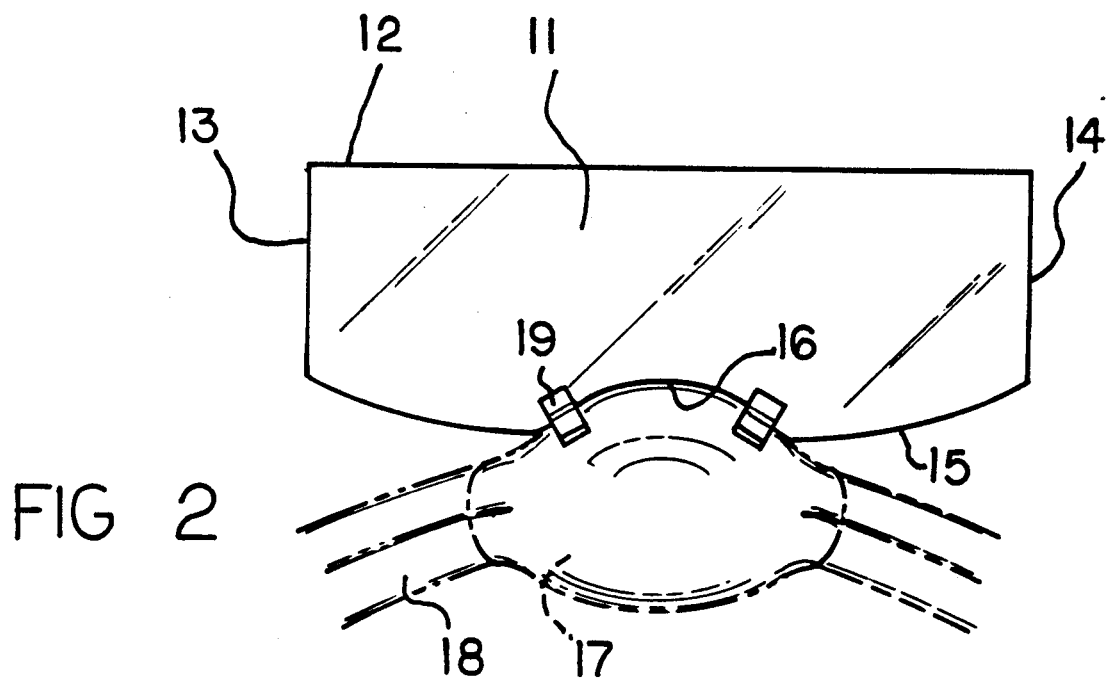
FIG. 2 is an enlarged orthographic view of the invention.
Figure 3:
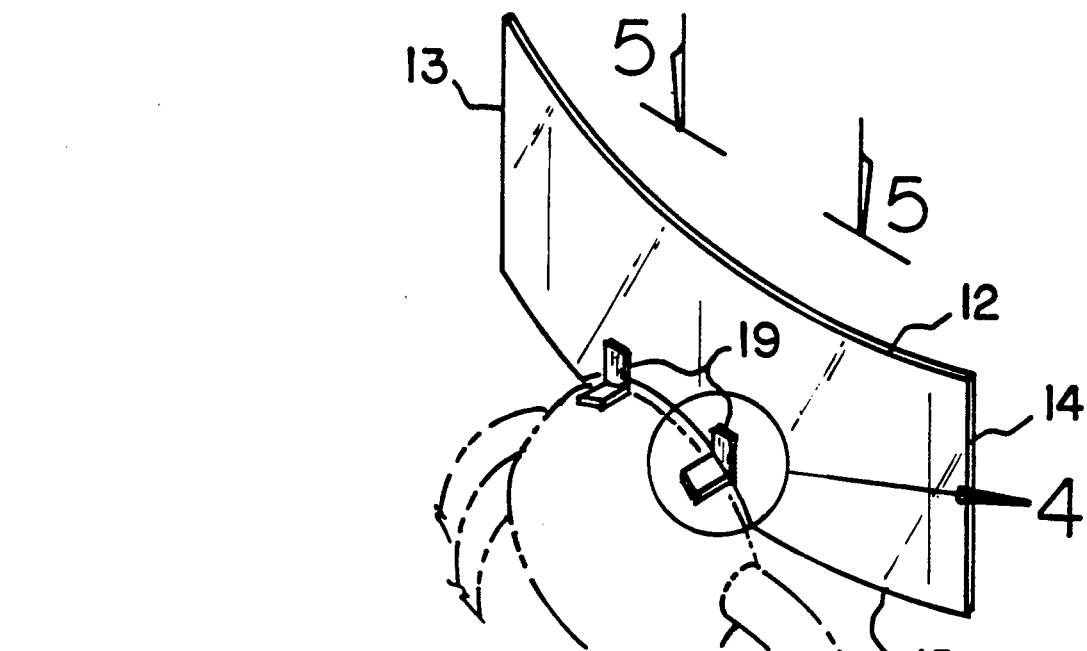
FIG. 3 is an isometric illustration of the invention.
Figure 4:
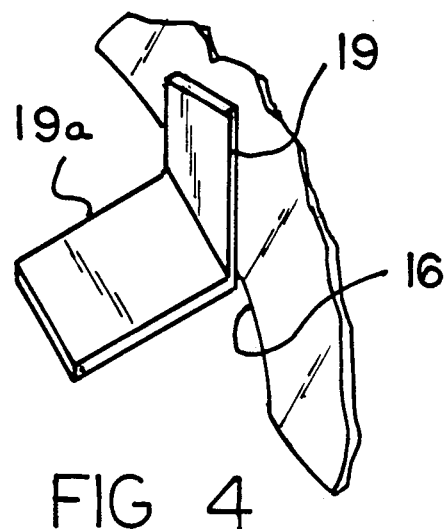
FIG. 4 is an isometric illustration of section 4 set forth in FIG. 3.
Figure 5:
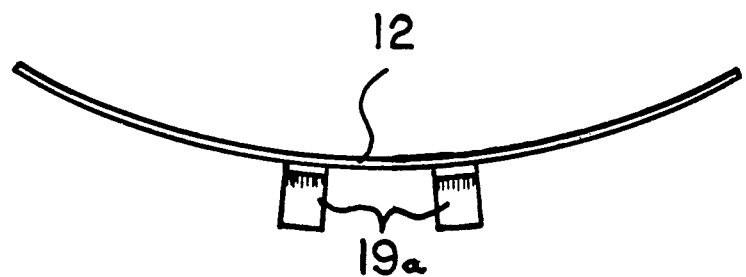
FIG. 5 is an orthographic view, taken along the lines 5—5 of FIG. 3 in the direction indicated by the arrows.

With reference now to the drawings, and in particular to FIGS. 1 to 10 thereof, a new and improved dental eye shield apparatus embodying the principles and concepts of the present invention and generally designated by the reference numeral 10 will be described.

More specifically, the dental eye shield apparatus 10 of the instant invention essentially comprises a polymeric flexible arcuate shield plate 11 formed of a transparent material, including a linear top edge 12 and including respective first and second side edges 13 and 14 arranged in a spaced relationship relative to one another and extending downwardly relative to the top edge 12. A convex lower edge 15 extends from lower distal ends of the first and second side edges 13 and 14 and includes a concave recess 16 oriented medially of the convex lower edge 15 projecting into the shield plate 11 to accommodate an individual's nose therewithin. A nasal mask 17 in pneumatic communication with a source of dental gas, such as nitrous oxide, includes pneumatic hoses 18 directed into the nasal mask, with the nasal mask 17 having its outer surface secured to the shield plate 11, and more specifically within the concave recess 16 by a plurality of L-shaped support tabs 19, with each support tab including an adhesive surface 20 for securement of and mounting to the outer surface of the nasal mask 17, with the adhesive surface 20 secured to a lower leg 19a of each support tab 19.

The use of a modified shield plate 11a further includes a flexible web 22 mounted to the shield plate's outer surface 21, with the flexible web 22 including a gelatinous coating 23 mounted coextensively to the flexible web 22 to receive and arrest airborne particles within the gelatinous coating 23 resultant from a dental procedure. Such particles are typically of tooth and/or filling structure such as to include silver and the like and may be subsequently disposed of by removal of the flexible web 22, in a manner as illustrated in FIG. 6, as the flexible web 22 is adhesively secured by transparent adhesive to the shield plate's outer surface 21.

Figure 9:
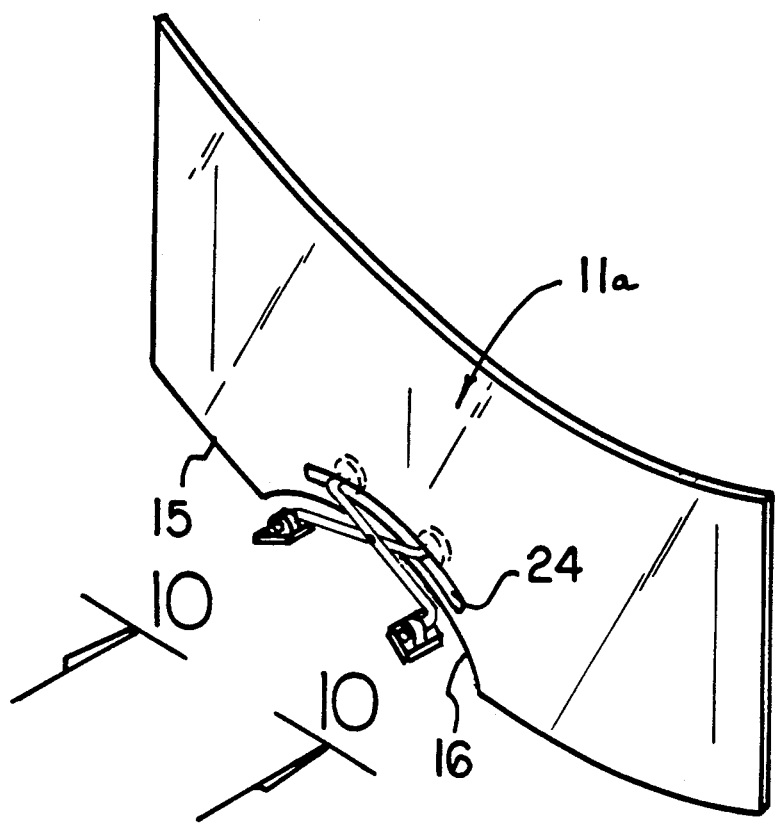
FIG. 9 is an isometric illustration of the invention including an adjustable nasal support structure.
Figure 10:
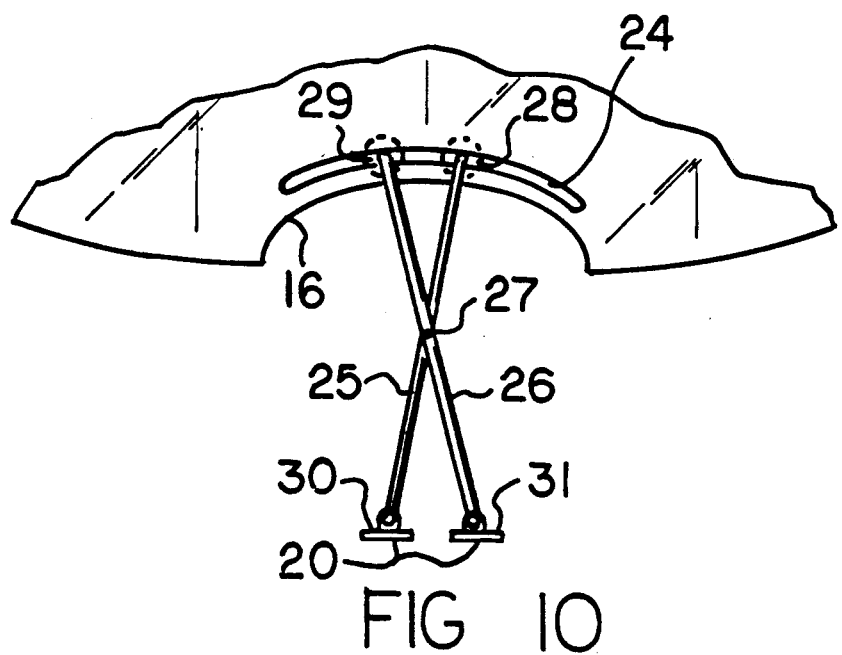
FIG. 10 is an orthographic view, taken along the lines 10—10 of FIG. 9 in the direction indicated by the arrows.

The shield plate 11a further includes in the apparatus illustrated in FIGS. 9 and 10 an arcuate slot 24 directed through the shield plate 11 in spaced adjacency to the concave recess 16. A first link and a second link 25 and 26 respectively are pivotally joined relative to one another by a link axle 27 intermediate the first and second link end portions. A first link guide chute 28 and a second link guide chute 29 are mounted to the upper distal end of the first and second links 25 and 26 and secure the upper ends of the first and second links within the arcuate slot 24. Lower distal ends of the first and second links include respective first and second link mounting feet 30 and 31, with the mounting feet 30 and 31 including the aforenoted adhesive surface 20, with the adhesive surfaces 20 oriented substantially orthogonally relative to the first and second links 25 and 26 to permit accommodation of masks of various geometric configurations.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental eye shield apparatus, comprising, a polymeric flexible shield plate of an arcuate configuration formed of a transparent material, including a linear top edge and formed with a first side edge spaced from a second side edge, a first side edge lower distal end and a second side edge lower distal end with a convex lower edge extending therebetween, wherein the convex lower edge includes a concave recess oriented medially of the convex lower edge to accommodate an individual's nasal region therewithin, and the concave recess further including a nasal mask secured within the concave recess, the nasal mask including pneumatic hoses in pneumatic communication with the nasal mask, and a first link mounting foot and a second link mounting foot mounted relative to the concave recess, wherein the first mounting foot and the second mounting foot each include an adhesive surface for adhesively securing the nasal mask thereto, and an arcuate slot directed through the shield plate adjacent the concave recess, wherein the arcuate slot includes a first link and a second link, the first link including a first link upper distal end and the second link including a second link upper distal end, the first link upper distal end includes a first link guide chute, the second link upper distal end includes a second link guide chute, with the first link guide chute and the second link guide chute mounted for sliding securement within the arcuate slot, and the first link and the second link include a link axle directed through the first link and the second link in an orthogonal relationship to pivotally mount the first link relative to the second link, and wherein said first link mounting foot is mounted to a lower distal end of the first link and said second link mounting foot is mounted to a lower distal end of the second link.

2. An apparatus as set forth in claim 1 wherein the shield plate includes a shield plate outer surface spaced from a shield plate inner surface, with the shield plate inner surface arranged for positioned adjacency relative to an individual's facial region and the shield plate outer surface includes a flexible web coextensively, adherably, and removably mounted to the shield plate outer surface, the flexible web includes a gelatinous coating coextensively secured to the flexible web to receive and arrest airborne particles within the gelatinous coating from a dental procedure.

* * * * *